US00PP13842P29

(12) United States Plant Patent
Holtkamp, Sr.

(10) Patent No.: US PP13,842 P2
(45) Date of Patent: May 20, 2003

(54) AFRICAN VIOLET PLANT NAMED 'EVERHARMONY'

(75) Inventor: Reinhold Holtkamp, Sr., Nashville, TN (US)

(73) Assignee: International Plant Breeding AG, Lieberfeld (CH)

( * ) Notice: Subject to any disclaimer, the term of this patent is extended or adjusted under 35 U.S.C. 154(b) by 0 days.

(21) Appl. No.: 10/046,984

(22) Filed: Jan. 17, 2002

(51) Int. Cl.[7] ..... A01H 5/00
(52) U.S. Cl. ..... Plt./270
(58) Field of Search ..... Plt./270

*Primary Examiner*—Kent Bell
(74) *Attorney, Agent, or Firm*—Foley & Lardner

(57) ABSTRACT

A new and distinct cultivar of African Violet named 'Ever-Harmony' particularly characterized by its multiflorescence trait, white to very light pink flowers with darker pink around the green center and on some petal edges, wavy edges ending with a finely frilled greenish line that can be up to 2–3 mm, strong, upright flower stems that curve slightly toward the center to form a compact flower bouquet above the leaves, medium green, wavy and serrated, oval to heart-shaped leaves, vigorous and extra large growth habit, flowering 12–13 weeks after potting, and long-lasting and non-dropping flowers.

1 Drawing Sheet

LATIN NAME OF THE GENUS AND SPECIES OF THE PLANT CLAIMED

*Saintpaulia ionantha.*

VARIETY DENOMINATION

'EverHarmony'.

BACKGROUND OF THE INVENTION

The present invention comprises a new and distinct cultivar of African Violet plant, botanically known as *Saintpaulia ionantha*, and hereinafter referred to by the cultivar name 'EverHarmony'.

The new cultivar was referred to during the breeding and selection process by the designation 'R 28/4' and is a product of a planned breeding program. The new cultivar originated from a cross made by the inventor, Reinhold Holtkamp, Sr., in the controlled breeding program in Nasvhille, Tenn. The female, or seed parent was a cultivar designated 'P 40/9 white muflo. Bie' (unpatented). The male, or pollen parent was a cultivar designated 'Q 6/2' (unpatented). 'P 40/9 white muflo. Bie' was produced from plants derived from African Violet seeds insulated for six years in a weightless environment in space on the Long Duration Exposure Facility.

In comparison to the instant plant, the female parent is a cultivar having white flowers without the light green edge, compact and multiflorescent. The male parent is a cultivar having purple-red flowers with white edges, semi-double, frilled, and non-multiflorescent.

'EverHarmony' was discovered and selected by the inventor as a flowering plant within the progeny of the stated cross in a controlled environment in Nashville, Tenn. Asexual reproduction of the new cultivar by leaf cuttings, as performed by me at Nashville, Tenn., has demonstrated that the combination of characteristics as herein disclosed for the new cultivar are firmly fixed and retained through successive generations of asexual reproduction. The new cultivar reproduces true-to-type.

'EverHarmony' has not been observed under all possible environmental conditions. The phenotype may vary significantly with variations in environment such as temperature, light intensity and day length without any change in genotype. The following observations, measurements and values describe the new cultivar as grown in Nashville, Tenn. and Haffen, Germany under greenhouse conditions which closely approximate those generally used in commercial practice.

BRIEF SUMMARY OF THE INVENTION

The following characteristics have been repeatedly observed and are determined to be basic characteristics of 'EverHarmony', which in combination distinguish this African Violet as a new and distinct cultivar:

1) Multiflorescence trait;

2) A single crown will grow as large as 30–40 cm in diameter;

3) Strong, upright flower stems curving slightly toward the center;

4) Single violet-shaped, white to very light pink flowers with darker pink in the center and around some edges ending with a finely frilled greenish edge, which can be up to 2–3 mm particularly on the 2 smaller petals;

5) Each plant carries 10–14, and sometimes more, upright flower stems each of which carries 13–18, and sometimes more, flowers;

6) Long-lasting, non-dropping flowers;

7) Vigorous and compact growth;

8) Plant saleable 12–13 weeks after potting;

9) Seed capsules are visible above the petals;

10) Medium-green, wavy and serrated, oval to heart-shaped leaves; and

11) After maturity the flowers dry off, and remain on the peduncle without becoming infected by Botrytis.

The new cultivar is most similar to 'EverLove' (U.S. Plant patent application Ser. No. 10/046,748). Both cultivars have the same parents and display the multiflorescence trait, have the same extra large growth habit and same type leaves and flower shape with the greenish edge. However, 'EverLove' has bright purplish-red flowers with a wide light pink edge and finely frilled greenish edge and dark green leaves whereas 'EverHarmony' has bi-colored white to very light pink flowers with darker pink center and edges and medium green leaves.

BRIEF DESCRIPTION OF THE DRAWING

The accompanying color photographic drawing shows a typical plant of the new cultivar 'EverHarmony'. The colors appearing in the photograph are as true as possible with color illustrations of this type.

DETAILED BOTANICAL DESCRIPTION

In the following description, color references are made to The Royal Horticultural Society Colour Chart (R.H.S.), except where general colors of ordinary significance are referred to. Color values were taken under natural sunlight conditions at approximately 12 p.m. in Nashville, Tenn. Measurements were taken 16–18 weeks from potting, as grown in a 6" pot.

Parentage:

*Male parent.*—'Q 6/2'.

*Female parent.*—'P 40/9 white muflo. Bie'.

Propagation: Leaf cuttings.

Plant: 10 cm to 13 cm tall when grown in pots, and 30–40 cm in diameter when fully grown.

*Leaves.*—General form: Oval to heart-shaped. Size: 80–90 mm wide and 85–95 mm long.

*Texture.*—Leather-like. Aspect: Wavy, serrated, hairy, shiny. Veins: Upperside: yellow-green, RHS 147 A; underside: well pronounced, light green, RHS 147 D, shiny. Color (upperside): Yellow-green RHS 147 A. Color (underside): Greyed-green RHS 194 C to RHS 194 D. Petiole: Strong, light green, RHS 147 C, hairy.

*Flowers.*—Buds: Bell-shaped, light green, between RHS 147 D and RHS 145 C, 8–10 mm in length, and 7–8 mm in width just before opening. Sepals: Five (5), one sepal for each flower petal; spear shaped, 4–6 mm in length, 1.5–2 mm in width at the tips; margins are straight, color: upperside and underside green, between RHS 147 B and RHS 146 C. Calyx: Shape: Funnel-shaped. Peduncle: Character: Strong upright, hairy; 20–25 mm in length. Color: green RHS 147 C with brownish touch RHS 177 A.

*Individual flowers.*—Size: 35–40 mm in width (as measured when pressed flat), 35–40 mm in length (as measured from the top of the small petals to the bottom of the large middle petal) Shape: Single violet-shaped with finely frilled, wavy edge. Petals: 5 (3 large, 2 small); small petals are 14–17 mm in length and 15–18 mm in width; large petals are 17–20 mm in length and 18–22 mm in width; margins are wavy and finely frilled; rounded apex shape. Color (upperside): The main color is between white and closest to but lighter than purple RHS 78 D, with tinges of color between purple RHS 78 D to RHS 78 C and red-purple RHS 74 D around center and around the edges. The center is yellow-green RHS 145 B and the fine frilled line is yellow-green RHS 145 B to RHS 145 C to RHS 145 D and can extend to 2–3 mm particularly on the 2 smaller petals. Occasionally, the green edge is lacking. Under cooler temperatures and more intensive lighting, the light pink tends to intensify. Color (underside): White to lighter than but closest to purple RHS 78 D; occasional green edge yellow-green RHS 145 B to RHS 145 C. Borne: Each of the flower stems carries 13–18 and more flowers on strong, upright peduncles that are free standing above the leaves, thereby forming a compact bouquet. Flowering habit: Flowers 12–13 weeks after potting. Lastingness of the individual bloom: 4–6 weeks under good growing conditions.

*Reproductive organs.*—Stamens: Two (2). Anthers: 2 composed of 4 anther cells, seed capsules push slightly through. Pistil: 1. Filaments: Yellowish white, 3–4 mm long. Pollen Color: Yellow RHS 7 A, moderate production. Styles: 6–7 mm long, pink, base of ovary light green and hairy.

*Roots.*—Normally developed, white when young, turning slightly brownish when older.

Disease resistance: 'EverHarmony' has shown very good resistance to all major violet diseases.

General observations: 'EverHarmony' is a very attractive cultivar due to its abundance of white to very light-pink flowers with darker pink around the green center and on some petal edges ending with a finely frilled greenish edge, which can be up to 2–3 mm particularly on the 2 smaller petals. Furthermore, it is an outstanding cultivar due to its multiflorescence trait in which a plant has 2 to 3 flower stems emerging out of each leaf internode, thereby continuously giving the cultivar new buds before the old flowers have wilted. A nice flower bouquet that is free-standing above the leaves develops 12–13 weeks after planting an unrooted plantlet. Under ideal growing conditions, 'EverHarmony' is never without blooms. Each of the 10–14, or more, strong flower stems carries 13–18, or more single violet-shaped flowers with wavy, frilled edges. 'EverHarmony' is an extra large cultivar, designed to be grown in a 15 cm pot. The plant may also be grown in a 10 cm pot successfully within a 8–10 week time period from potting to finish. The profuse bouquet is surrounded by large, medium-green, oval to heart-shaped, wavy and serrated leaves. The flowers are long-lasting and non-dropping and the seed capsules push slightly through.

I claim:

1. A new and distinct African Violet plant named 'EverHarmony', as described and illustrated herein.

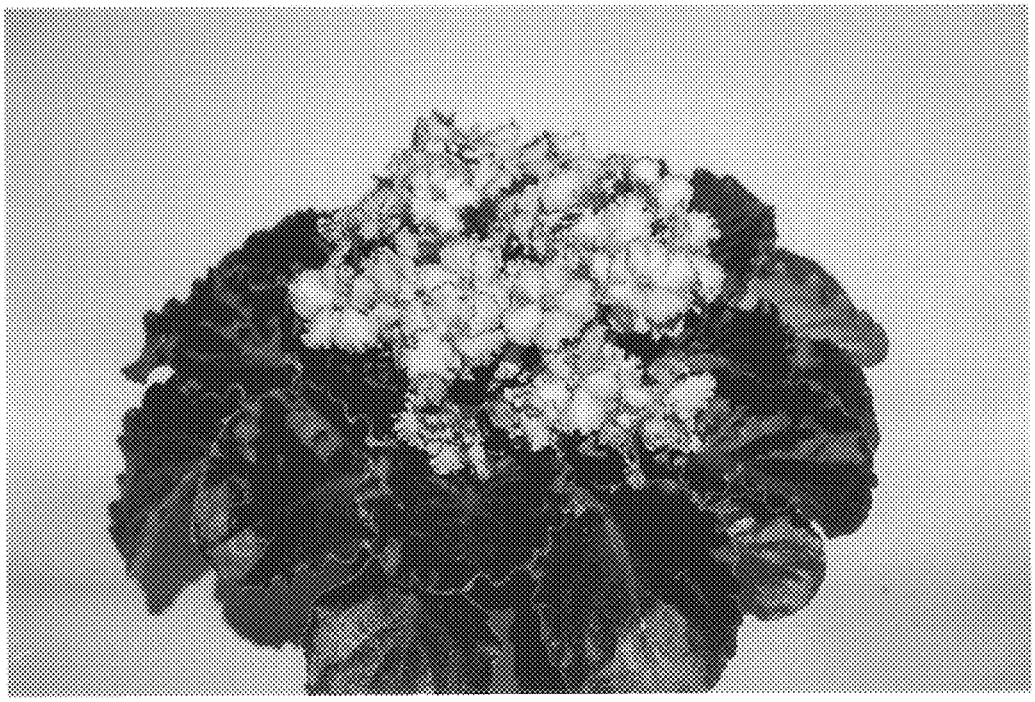

* * * * *